(12) United States Patent
Levine et al.

(10) Patent No.: US 7,993,385 B2
(45) Date of Patent: Aug. 9, 2011

(54) METHOD AND APPARATUS FOR CAGED STENT DELIVERY

(75) Inventors: Marc-Alan Levine, San Francisco, CA (US); Stephen Hebert, Berkeley, CA (US)

(73) Assignee: Counter Clockwise, Inc., Palo Alto, CA (US)

( * ) Notice: Subject to any disclaimer, the term of this patent is extended or adjusted under 35 U.S.C. 154(b) by 921 days.

(21) Appl. No.: 11/590,946

(22) Filed: Nov. 1, 2006

(65) Prior Publication Data

US 2007/0088423 A1     Apr. 19, 2007

Related U.S. Application Data

(63) Continuation of application No. 10/286,109, filed on Nov. 1, 2002, now Pat. No. 7,169,172.

(51) Int. Cl.
*A61F 2/06* (2006.01)

(52) U.S. Cl. ....................... 623/1.12; 623/903

(58) Field of Classification Search .............. 623/1.11, 623/1.12, 1.2, 1.13, 903; 606/108, 110, 113, 606/127, 194, 198, 200; 604/104–109
See application file for complete search history.

(56) References Cited

U.S. PATENT DOCUMENTS

| | | | |
|---|---|---|---|
| 3,517,128 A | 6/1970 | Hines | |
| 4,990,151 A | 2/1991 | Wallsten | |
| 5,098,440 A | 3/1992 | Hillstead | |
| 5,195,506 A * | 3/1993 | Hulfish | 600/204 |
| 5,453,090 A | 9/1995 | Martinez et al. | |
| 5,456,667 A * | 10/1995 | Ham et al. | 604/107 |
| 5,464,408 A | 11/1995 | Duc | |
| 5,474,563 A * | 12/1995 | Myler et al. | 606/108 |
| 5,618,300 A * | 4/1997 | Marin et al. | 623/1.11 |
| 5,649,906 A * | 7/1997 | Gory et al. | 606/108 |
| 5,910,144 A | 6/1999 | Hayashi | |
| 6,132,389 A * | 10/2000 | Cornish et al. | 600/585 |
| 6,187,016 B1 | 2/2001 | Hedges et al. | |
| 6,217,585 B1 | 4/2001 | Houser et al. | |
| 6,254,628 B1 | 7/2001 | Wallace et al. | |
| 6,280,465 B1 * | 8/2001 | Cryer | 623/1.11 |
| 6,468,298 B1 | 10/2002 | Pelton | |
| 6,508,825 B1 | 1/2003 | Selmon et al. | |
| 6,514,280 B1 | 2/2003 | Gilson | |
| 6,558,404 B2 * | 5/2003 | Tsukernik | 606/198 |
| 6,802,846 B2 | 10/2004 | Hauschild et al. | |
| 6,830,575 B2 * | 12/2004 | Stenzel et al. | 606/108 |
| 6,945,989 B1 * | 9/2005 | Betelia et al. | 623/1.11 |
| 7,063,707 B2 * | 6/2006 | Bose et al. | 606/127 |
| 7,235,093 B2 * | 6/2007 | Gregorich | 623/1.11 |
| 2001/0047150 A1 * | 11/2001 | Chobotov | 604/107 |
| 2002/0082639 A1 * | 6/2002 | Broome et al. | 606/200 |
| 2002/0161427 A1 | 10/2002 | Rabkin et al. | |

* cited by examiner

*Primary Examiner* — Elizabeth Houston

(57) ABSTRACT

The method and apparatus for caged stent delivery is provided herein. The device can be used to position and deliver any type of stent to a preselected treatment site within an intraluminal cavity. The device comprises a tubular portion, a plurality of arms attached to the distal end of the tubular portion, and a mechanism to open the arms. In operation, the caged device carries a stent in a constricted form to the treatment site for deployment. The arms of the cage are then opened, the stent released and deployed, and the device withdrawn. Several methods are provided to open the arms, including various pullwires, a piston, an electrolytic joint, and an activator. The arms may be constructed of a shape memory alloy and opened when shape memory behavior is effected. The device may be used with conventional catheters or used with a stent-loaded guidewire.

18 Claims, 13 Drawing Sheets

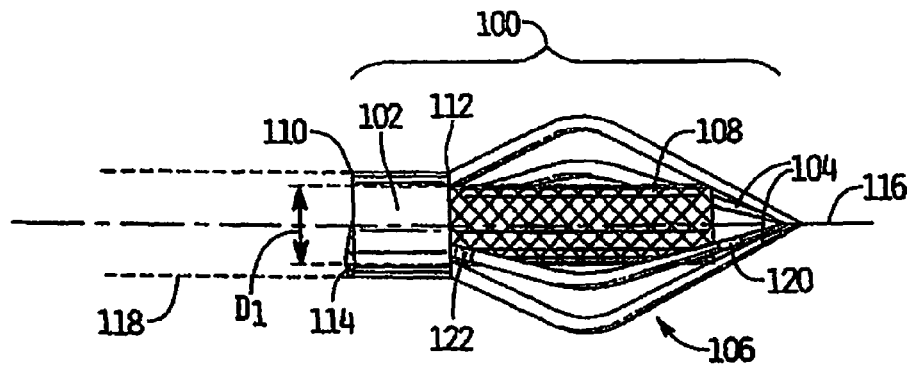
FIG_1
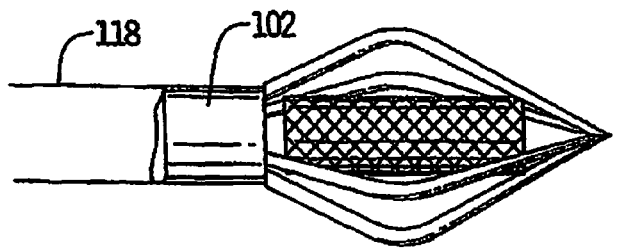
FIG_2A
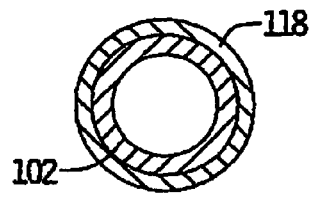
FIG_2B
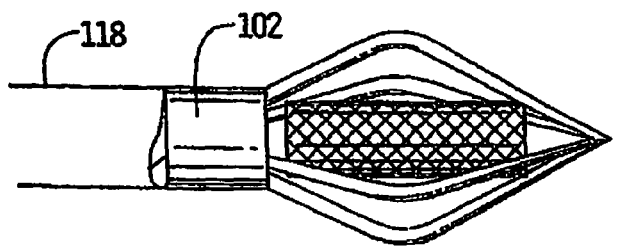
FIG_2C

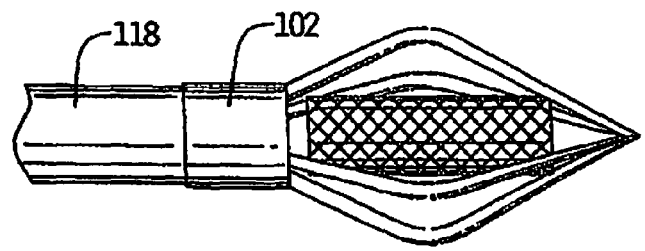
FIG_2D
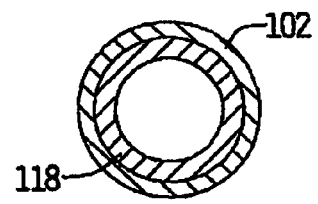
FIG_2E
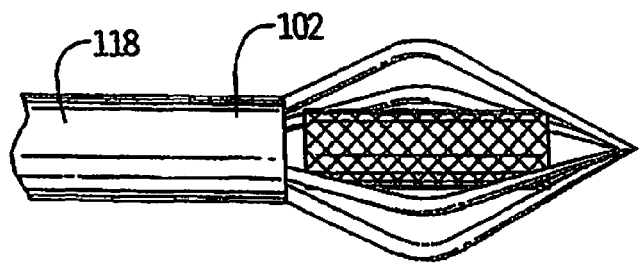
FIG_2F
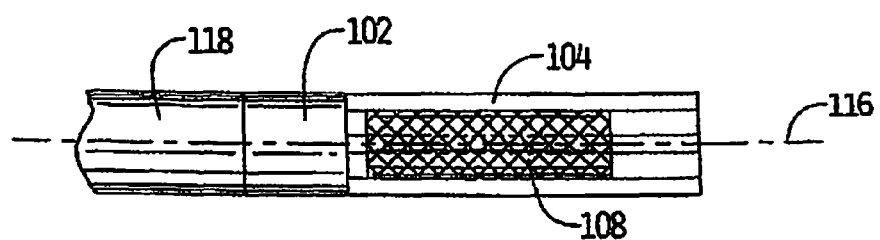
FIG_3A

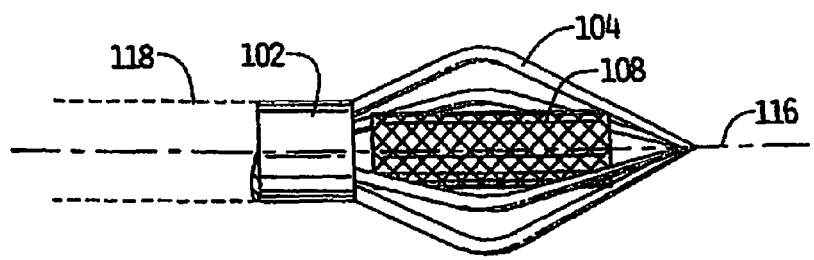
FIG_3B
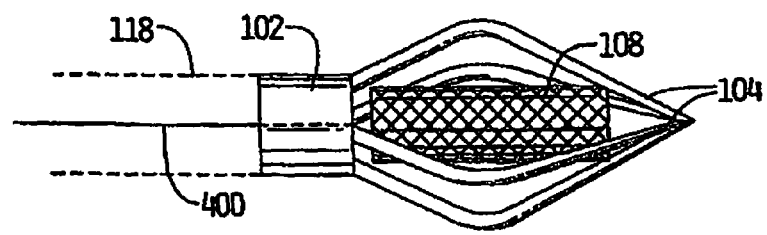
FIG_4A
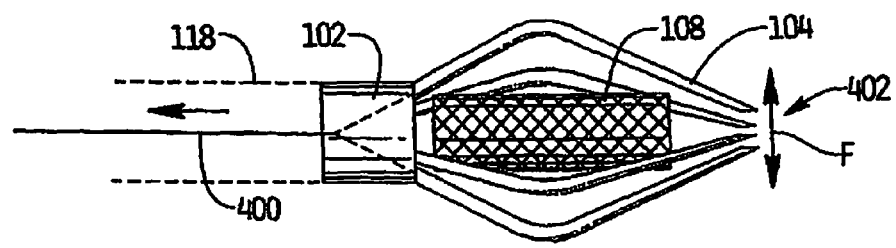
FIG_4B

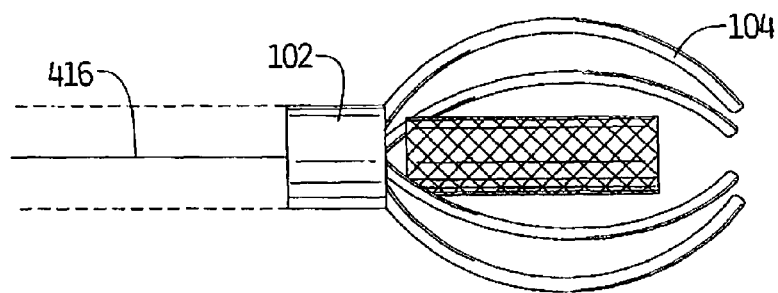
FIG_4I
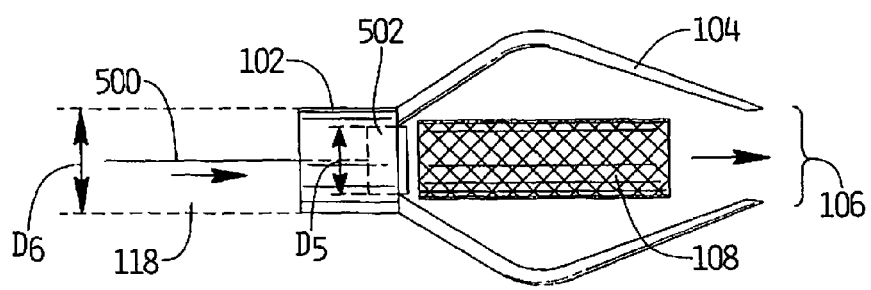
FIG_5
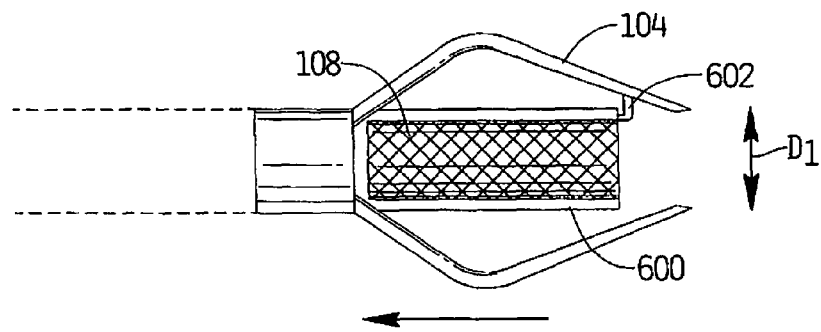
FIG_6A

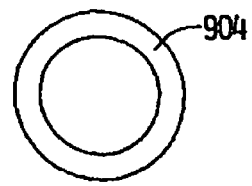
FIG_9C
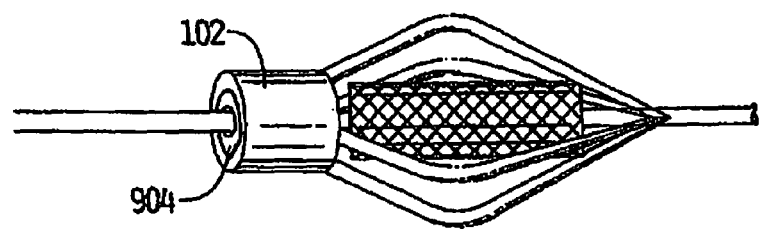
FIG_9D
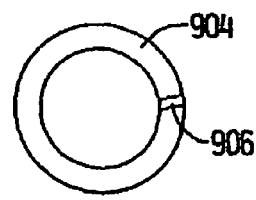
FIG_9E
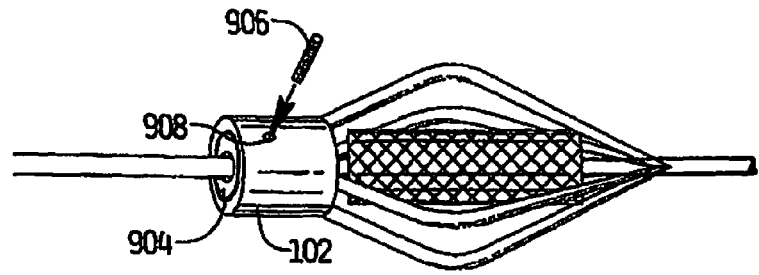
FIG_9F

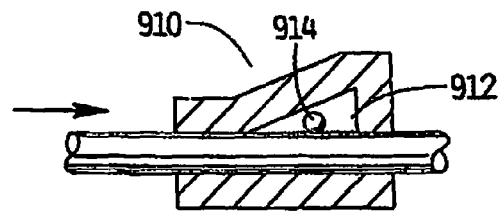
FIG_9G
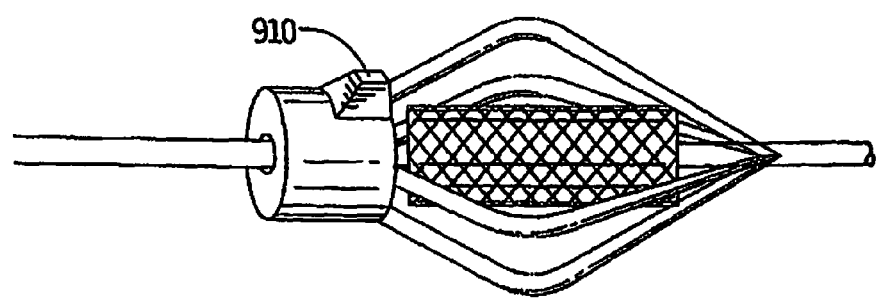
FIG_9H
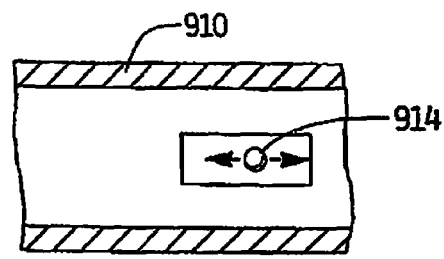
FIG_9I

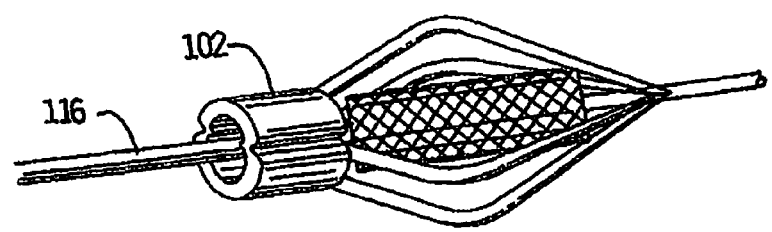
FIG_9J
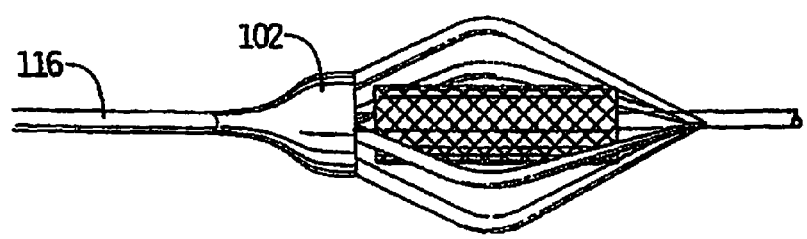
FIG_9K
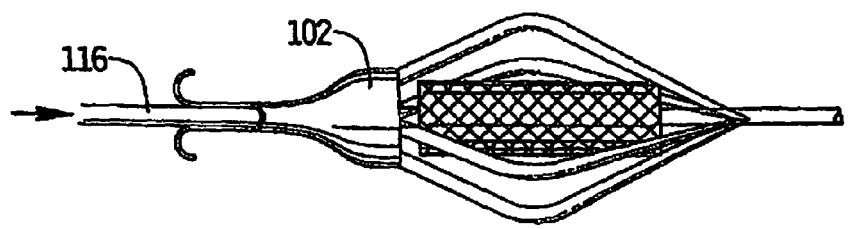
FIG_9L

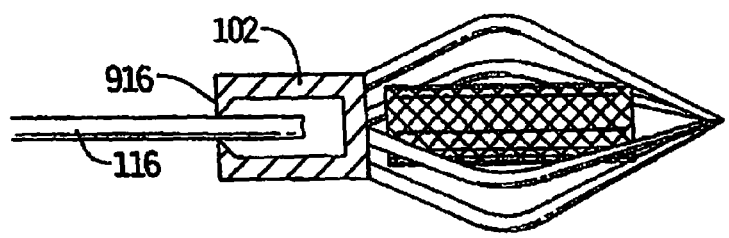
FIG_9M
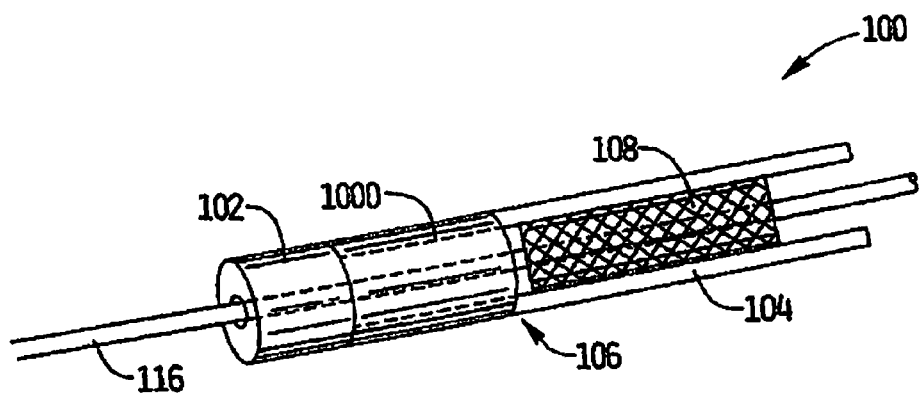
FIG_10
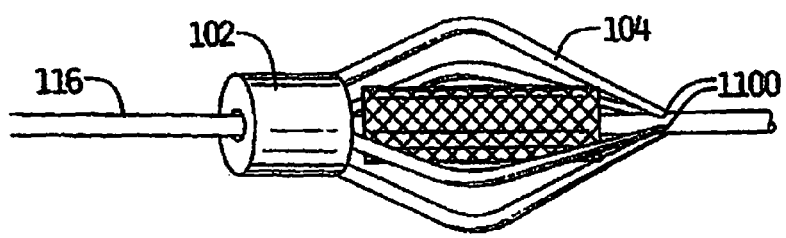
FIG_11

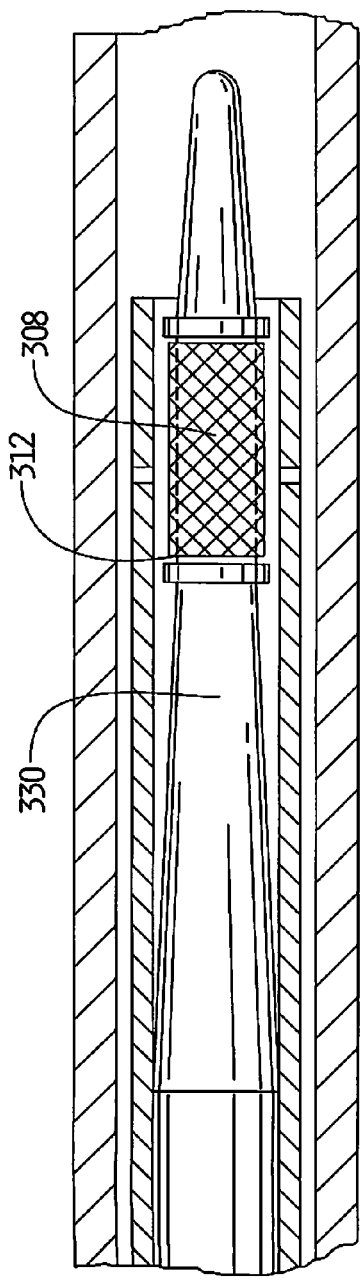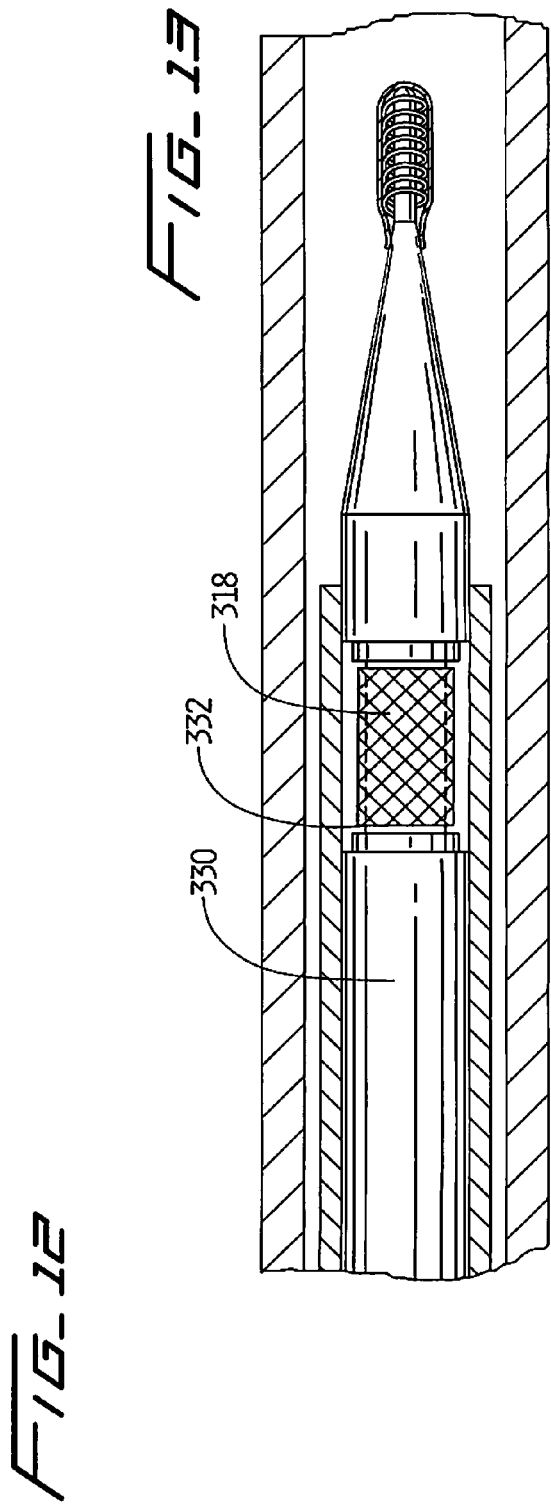

METHOD AND APPARATUS FOR CAGED STENT DELIVERY

This application is a continuation of application Ser. No. 10/286,109, filed Nov. 1, 2002 now U.S. Pat. No. 7,169,172. The entire contents of this application is incorporated herein by reference.

FIELD OF THE INVENTION

The present invention relates to methods for delivering implantable objects within a body cavity. More particularly, the invention relates to an apparatus and method for positioning a stent or graft intraluminally within a target vessel.

BACKGROUND OF THE INVENTION

Stents are often employed in a variety of patient treatment and diagnostic procedures. They are usually implanted within blood vessels, biliary ducts and other body lumens to maintain their passageways. For example, a radially self-expanding stent can be deployed in an artery following a percutaneous transluminal coronary angioplasty (PTCA) procedure or a percutaneous transluminal angioplasty (PTA) procedure. The stent resists a tendency in the vessel to close, thus countering acute reclosure and plaque restenosis. A variety of stents, and methods for delivering them, are disclosed in the prior art.

One method frequently described for delivering a stent to a desired intraluminal location includes mounting and crimping the expandable stent on the expandable member of a catheter, such as a balloon, which is provided on its distal end. The catheter is advanced to the desired location within the patient's body lumen and the balloon is subsequently inflated to expand the stent into a permanent expanded condition and then the balloon is deflated and the balloon and catheter removed from the body lumen leaving the stent permanently implanted.

Another method frequently described for delivering a stent to a desired intraluminal location includes mounting the stent on the distal end of a catheter, where the stent is a self-expanding stent formed from self-expanding stainless steel, or shape memory alloys such as nickel titanium (NiTi). The self-expanding stents are implanted by advancing the catheter to the desired location within the patient's body lumen, withdrawing a sheath so that the stent can self-expand into the body lumen, and then withdrawing the catheter and sheath leaving the stent implanted.

Regardless of the stent type, its deployment frequently involves guiding a catheter or other delivery appliance through convoluted paths defined by arteries or other body passages. A well known technique for guiding the delivery catheter includes initially positioning a guidewire along the desired path, with the distal end of the guidewire near the treatment site and a proximal portion of the guidewire remaining outside of the body. The delivery catheter has a lumen that runs throughout its length. The distal end of the delivery catheter is threaded onto the proximal end portion of the previously positioned guidewire so that it may be advanced distally over the guidewire, ultimately to the treatment site for stent deployment.

Procedures that employ guidewires often require exchanging of treatment appliances. This exchange of catheters usually requires that the proximal portion of the guidewire be protruding from the patient's body and be longer than any catheter involved in the procedure. Because of the difficulty created in maneuvering the guidewire and catheters and the substantial frictional force generated by the guidewire and catheter interaction, rapid exchange methods have been developed. These rapid exchange methods are well known in the art.

However, despite the improvements in the stent technology heretofore developed, there remains a need for greater control in stent delivery. There also remains a need for devices that can deliver stents throughout the body, to the smallest of intraluminal cavities. Unfortunately, many of the stent delivery methods disclosed still require use of a catheter and a guidewire to deliver the stent to a particular site, even if their exchange is made easier. Furthermore, many prior art stent delivery methods require that the stent be surrounded by a grip or a sheath, or be expanded with use of a balloon catheter, or the like.

One of the problems encountered in using these prior art stents is the inability to tightly crimp the stent, either on the balloon portion of the catheter, or onto its distal end. However, because it is still desirable that the stent have a small diameter for delivery purposes, yet be able to expand to various diameters to hold open the lumen after implanting, better delivery devices and methods are needed. No methods exist that provide a caged stent delivery system. Further, no methods exist that provide a caged stent delivery system that is adaptable for use with a guidewire and catheter combination, or a guidewire alone.

BRIEF SUMMARY OF THE INVENTION

The present invention fills the voids of the prior art by providing a method and apparatus for caged stent delivery that affords greater control and greater access to intraluminal cavities having small circumferences. The device of the present invention delivers the stent to an intraluminal site and controllably releases it for expansion within the lumen. The device comprises a tubular portion, a plurality of arms that are attached to the distal end of the tubular portion, and a mechanism for opening the arms. Any number of arms may be used. The arms may be of any appropriate length, have any number of angle configurations, and be constructed from any number of materials. In one variation, there are at least two arms, which are made of a shape memory alloy. The arms may have radio-opaque markers located at a position along their length to allow for tracking of the stent location or may be entirely comprised of radio-opaque material. Together, these arms define a cage for containing the stent in a constricted form, having a smaller diameter than when deployed within a body cavity lumen. The cage may further be collapsible and expandable.

In operation, the cage carries a stent, in its smaller diametric form, to the site of deployment within a lumen of the body. The cage arms are then opened and the stent released. Any number of methods may be used to open the arms defining the cage. In some variations, mechanical methods are employed, such as a pullwire, a piston, or a spring. In others, sensors or electrolytic joints are employed. The stent may then be pushed from the cage (e.g. using a piston or pressurized saline solution) to a desirable position within the body lumen. Alternatively, the stent may simply be released and the caged device withdrawn. The stent is then deployed and expanded to its final diameter.

The device has a tubular portion where the arms attach, which may be configured such that its proximal end is adaptable for use with any of the variously sized conventional catheters, a specially manufactured catheter, or even a single guidewire. The proximal end of the tubular portion may be adapted to fit within the lumen of a catheter, may be adapted to attach to the distal end of a catheter, may be positioned on the distal tip of the catheter, or may comprise a portion of the catheter itself.

Similarly, the tubular portion may be adapted to attach to a guidewire alone, which allows access to intraluminal spaces having very small circumferences. This is especially advantageous when trying to deliver stents to intracranial vessels where the catheter is often too large to fit therein. The tubular portion may be connected to the guidewire in any number of ways. For example, the tubular portion may be comprised of a low-temperature heat shrink material to constrict upon heating, thereby tightly attaching itself to the guidewire. Similarly, a locking collet (with or without a set screw), an internal socket (with or without a set screw), or a locking ball may be used. The tubular portion may also be attached to the guidewire by an adhesive (e.g., Loctite glue), or by crimping the tubular portion onto the guidewire using a hemostat or similar device. However, when a catheter is used, rapid exchange techniques can be employed to reduce exchange times and minimize friction between the guidewire and catheter.

Any type of stent may be used in combination with the present invention. For example, in some variations a radially self expanding stent (with or without an outer sheath) is employed. In other variations, use of the present invention with a balloon catheter is described. In this way, the caged stent delivery device and methods described herein are easily adaptable for use with stents currently used in the industry.

BRIEF DESCRITPION OF THE DRAWING

The foregoing and other aspects of the present invention will best be appreciated with reference to the detailed description in conjunction with the accompanying drawings, wherein:

FIG. 1 provides an illustration of the caged stent delivery device of the present invention.

FIGS. 2A and 2B provides an illustration where the tubular portion of the caged stent delivery device is adapted to fit within the lumen of a catheter.

FIG. 2C provides an illustration where the tubular portion of the caged stent delivery device is adapted to attach to the distal end of the catheter.

FIGS. 2D and 2E provide an illustration where the tubular portion of the caged stent delivery device is positioned on the distal tip of the catheter.

FIG. 2F provides an illustration where a catheter itself comprises the tubular portion of the caged stent delivery device.

FIGS. 3A and 3B provides an illustration of the cage of the present invention having an expandable and collapsible form.

FIGS. 4A and 4B show one variation of opening the arms of the cage of the present invention using a pullwire.

FIGS. 4H and 4I illustrate one variation where a rotatable pullwire is rotated about its axis to open the arms of the caged device.

FIG. 5 provides an illustration of how a stent may be pushed out distally from the caged device.

Figure 6B:
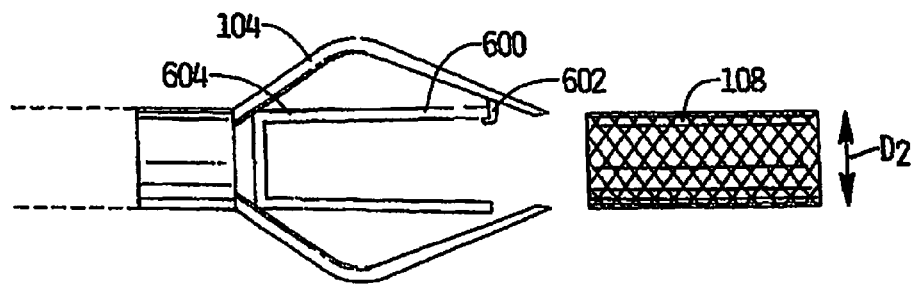

FIGS. 6A and 6B illustrate a method of how a sheathed, radially self expanding stent may be released and deployed using the present invention.

Figure 7:
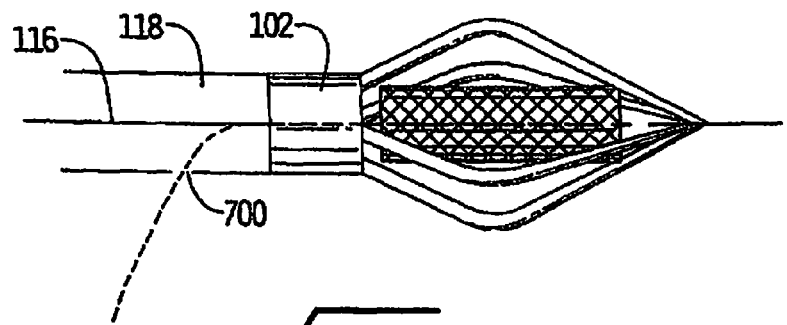

FIG. 7 illustrates how rapid exchange techniques may be used with the present invention.

Figure 8:
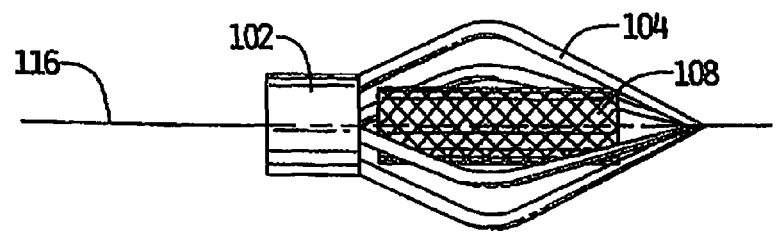

FIG. 8 provides an illustration of one variation of the present invention, where the caged device is attached to a guidewire and a catheter is not used.

FIGS. 9A-9M illustrate several variations of how the tubular portion of the present invention may be attached to a guidewire for use of the caged delivery device of the present invention without a catheter.

FIG. 10 illustrates one variation of how a stent-loaded guidewire may be used with the caged delivery device of the present invention and an outer sheath and FIG. 11 illustrates another variation of how a stent-loaded guidewire may be used with the caged delivery device of the present invention.

FIG. 11 illustrates another variation of how a stent-loaded guidewire may be used with the caged delivery device of the present invention.

FIGS. 12 and 13 illustrate cross-sectional views of alternate embodiments of the stent loaded on a reduced diameter guidewire portion.

DETAILED DESCRIPTION OF THE INVENTION

Turning now to the drawings, wherein like numerals indicate like elements throughout the views, there is shown in FIG. 1 a device 100 for caged delivery of a stent or graft within a body lumen. Device 100 is used to deliver a stent to an intraluminal site and to controllably release it for expansion within a body lumen. The device comprises a tubular portion 102, a plurality of arms 104 attached to the distal end of tubular portion 102, and a mechanism to open the arms. Together, the arms 104 define cage 106 for containing stent 108 in a constricted form, having a smaller diameter, D1, than when deployed within a body cavity lumen, D2.

In operation, cage 106 carries stent 108, in its smaller diametric form to a preselected treatment site for deployment within a lumen of the body. Arms 104 are then opened, allowing the stent to be released from the cage. As described in greater detail below, the stent may be pushed from the cage to the treatment site, or the stent may simply be released at the treatment site and the caged device withdrawn. The stent is then deployed as will be described in greater detail below.

Any number of arms 104 may be used to comprise cage 106. However, there should be a minimum number of arms such that they comprise a cage that can contain the stent in its smaller diametric form. This may require there be at least two arms. However, it is not without possibility that the cage be comprised of one arm alone, bent and manipulated in such a way to enable a stent to be encapsulated therein.

The arms may be of equal length, or may be of different lengths. Having one arm longer than the others may help facilitate the controlled release of the stent as the arms are sequentially released. In a like fashion, the arms may have any number of angle configurations depending on the stent release and deployment properties desired. The angle may be of any degree and may be located at any distance along the length of the arms. Similarly, the arms may have multiple angles at multiple locations.

Any number of materials may be used to construct arms 104. However, since they will be in contact with body cavities, the material selected should be non-toxic. For example, arms 104 may be constructed of stainless steel, of the same material used to construct an optional catheter, of the same material used to construct the guidewire, or as described in greater detail below, shape memory alloys. Further, radio-opaque marker bands may optionally be placed on arms 104 of cage 106, either distally 120 or proximally 122 of stent 108 to visually aid in its placement, as shown in FIG. 1. Alternatively, distal and proximal marker bands 120 and 122 may be eliminated altogether. Additionally, the arms 104 may be constructed of radio-opaque material.

Tubular portion 102 has a proximal end 110, a distal end 112, and a lumen 114 defined therethrough. It may be configured such that its proximal end 110 is adaptable for use with any of the variously sized conventional catheters, a specially manufactured catheter, or even a single guidewire. For example, the proximal end of tubular portion 102 may be adapted to fit within the lumen of a catheter (FIGS. 2A), may be adapted to attach to the distal end of a catheter (FIG. 2B), may be positioned on the distal tip of the catheter (FIG. 2C), or may comprise a portion of the catheter itself (FIG. 2D). Similarly, as will be described in greater detail below, the tubular portion may be adapted to attach a guidewire 116 alone.

Guidewire 116, having a proximal end and a distal end, may be inserted through the lumen of an optional catheter 118, through the lumen of tubular portion 102 and further through the cage 106, extending distally past it. Alternatively, guidewire 116 may be adapted to attach to tubular portion 102 without the use of optional catheter 118. The guidewire 116 may be a conventional guidewire or it may be formed from a hypotube. The hypotube or guidewire may be made from a variety of materials such as superelastic metals, platinum, or from metals such as stainless steel.

Arms 104 may be rigid, or may be flexible to allow cage 106 to be expandable and collapsible, as shown in FIGS. 3A and 3B, for further restraining the stent therein. The cage encapsulates the stent, and in one variation this is accomplished by providing cage arms that extend distally over the distal portion of the stent. In another variation, this is accomplished by providing arms that are woven in between the interstitial spaces of the stent. The arms may be opened such that they can release the stent contained therein for deployment within an intraluminal cavity.

For example, the distal most tip of arms 104 may comprise an electrolytic joint, which when activated, releases the arms of the cage for deployment of the stent. Similarly, any type of activator may be placed on the arms of the cage to control the opening of arms 104. This activator may be in further communication with, and be controllable by, a processor located outside the patient's body. In this way, a surgeon who is monitoring the stent location (e.g., using radio-opaque markers) may enter a command in the processor to release the arms when the stent reaches the desired site of deployment. In one variation, an activator made of Nitinol is used to control the release of arms 104. Guidewire 116 may comprise a heating element or provide a mechanism to induce stress, thereby causing the shape memory effect necessary to plastically deform the activator and thus release the arms. In a similar manner, arms 104 themselves may be constructed of Nitinol. Again, guidewire 116 may provide the heat or stress elements necessary to plastically deform the arms, thereby releasing the stent. However it should be noted that when the stent itself is comprised of Nitinol, special care should be taken to select Nitinols of different Nickel-Titanium compositions. In this way, the arms may be timed to release prior to the beginning of stent expansion.

Figure 4C:
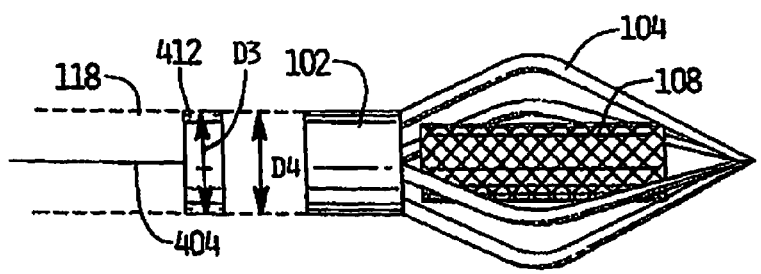
FIGS. 4C and 4D show how a piston and optional pressure sensors may be employed to open the arms of the caged device of the present invention.
Figure 4D:
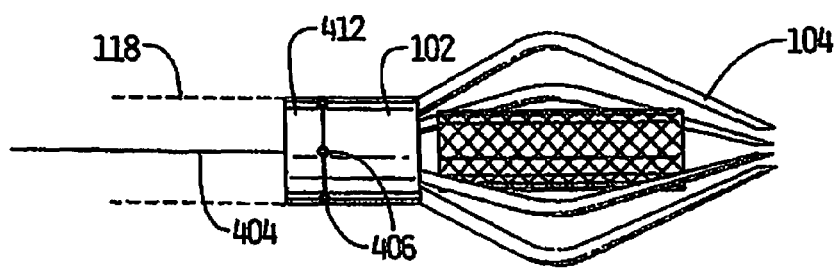

Mechanical methods may also be used to release the cage arms, as shown in FIGS. 4A-4E. In one variation, a movable pullwire is used as shown in FIGS. 4A and 4B. Pullwire 400 may run through the entire lumen length of an optional catheter 118 and be configured such that when engaged, a radial force 402 is exerted on the arms, thereby releasing them as shown in FIG. 4B. In another variation, a movable piston or plunger is used to release arms 104. This variation is shown in FIGS. 4C and 4D. In FIG. 4D, tubular portion 102 is attached to the distal tip of optional catheter 118. Piston 404 is disposed within optional catheter 118 and is pushed distally toward arms 104 such that when the piston head 412 contacts the proximal end of tubular portion 102, a radial force is exerted on the arms, thereby releasing them. The diameter of piston head 412 varies with, and is determined by, the diameter of the selected catheter. For example, the head may have a diameter, D3, slightly less than inner diameter, D4, of optional catheter 118 such that the piston head and inner catheter wall are in slidable contact with one another.

Another variation is shown in FIG. 4D, where piston 404 is moved distally toward tubular portion 102 until contact is made with pressure sensors 406 located thereon. Sensors 406 need not be located on the proximal end of tubular portion 102 as shown in FIG. 4D. They may be located at any distance along the tubular portion, provided that the piston is configured such that sufficient pressure is exerted on the sensors for them to detect a pressure change and trigger the release of the arms. The piston may be disposed through the entire lumen length of the optional catheter and exit at a remote proximal point external to the patient's body. Alternatively, the piston may be disposed only within the distal tip of the catheter and by controlled remotely. Both methods allow a surgeon who is monitoring the stent location (e.g. using radio-opaque techniques) to release the arms. The surgeon may distally push the piston forward manually, or alternatively, a processor may instead be used to control piston movement. In the later variation, the surgeon would enter a simple command in the processor to signal the release of the arms.

Figure 4E:
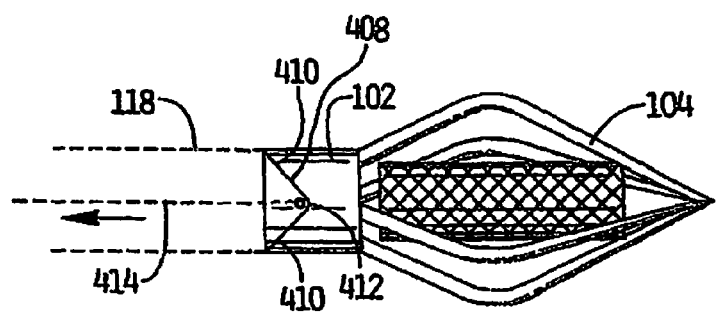
FIG. 4E illustrates one variation where a spring device is used to open the arms of the caged device.
Figure 4F:
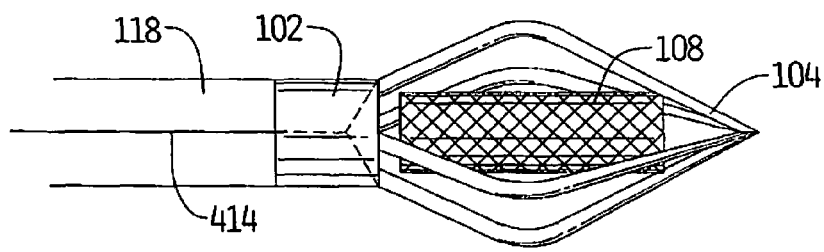
FIGS. 4F and 4G illustrate one variation where the arms are retracted proximally within the lumen of an optional catheter.
Figure 4G:
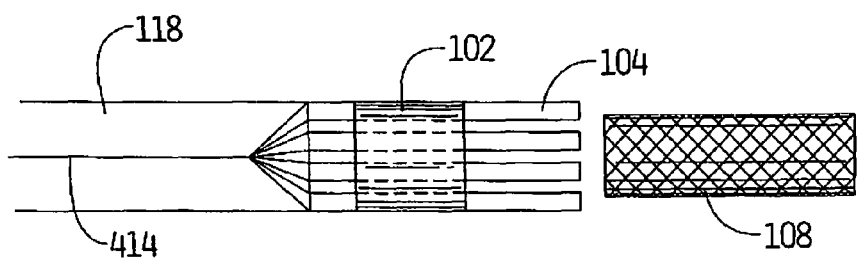
Figure 4H:
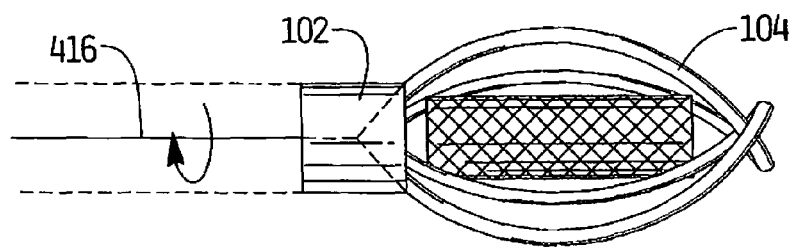

Another variation of the cage opening mechanism involves a spring configuration as shown in FIG. 4E. In this variation a spring is disposed within tubular portion 102. In the simplest of possible configurations, the spring 408 has two members 410 extending from an inner coil 412. The spring may be connected to a pullwire 414, or any similar devices, such that when the pullwire is pulled proximally, a downward force is exerted on members 410, compressing the coil and releasing arms 104. Other mechanisms that may be employed to open arms 104 are illustrated in FIGS. 4F and 4G. In FIG. 4F, for example, pullwire 414 is attached to arms 104 such that when it is pulled back proximally, arms 104 are retracted proximally within optional catheter 118. FIGS. 4G illustrates a variation where a rotatable wire 416 is disposed within the lumen of optional catheter 118 and is configured such that when it is rotated about its axis, arms 104 are opened. These wires may be controlled manually or automatically as described above. These methods of releasing the cage arms, however, are merely illustrative and it should be understood that any number of mechanisms for releasing arms 104 may be used. Such use is expressly contemplated by the present invention.

Once arms 104 are open, the stent may be pushed out for deployment within a body lumen or the arms may simply be retracted leaving the stent at a desired location. For example, as shown in FIG. 5, stent 108 may be pushed out of cage 106 by a piston or plunger 500. Piston 500, having head 502 at its distal end, is disposed within the optional catheter lumen. When piston 500 is pushed forward distally it enters lumen 114 of tubular portion 102 and gently contact and moves stent 108 distally out of cage 106. The diameter of piston head 502 varies with, and is determined by, the diameter of the selected catheter and its attachment to tubular portion 102.

For example, in one variation, tubular portion 102 and optional catheter 118 have inner walls flush with one another and have equal inner diameters. In this way piston head 502 may have a smooth transition from the catheter lumen through the lumen of tubular portion 102. Head 502 may then have a diameter, D5, slightly less than inner diameter, D6, of optional catheter 118 (and consequently tubular portion 102) such that the piston head and inner catheter wall are in slidable contact with one another. In another variation (not shown), the stent may be pushed out of the cage by discharging a pressurized saline solution through the lumens of the optional catheter and tubular member.

The caged delivery of the present invention may also be used to retract a stent when partially deployed if retraction of the stent prior to full deployment becomes desirable or necessary. In this way, the arms of the cage can recapture the stent prior to its full deployment within an intraluminal space. The caged delivery device can then be repositioned and the stent redeployed.

Any number of stent configurations may be used in combination with the present invention. For example, the stent may be made of a shape memory alloy and be intended to expand radially in vivo under the influence of shape memory behavior. Similarly, the stent may be made out of any number of materials and then deployed with the use of a balloon catheter.

In one variation, the stent is radially self-expanding. The stent expands from a constrained first configuration, having diameter D1, as when placed within the cage for delivery, to a larger expanded second configuration as when deployed within the vasculature, having diameter D2. The stent may be made of various materials, such as platinum, nickel, Nitinol, other shape memory alloys, or other self-expanding materials.

Similarly, the stent may be radially self-expanding and be further constrained by a sheath as shown in FIG. 6. When stent 108 is constrained by sheath 600, it has diameter D1. Stent 108 may be delivered to a treatment site within an intraluminal body cavity in its sheathed state and within the caged delivery device. In this variation, arms 104 of cage 106 may have at least one hook 602 for engaging the sheath. Arms 104 may be opened by any of the mechanisms described above. Then, as the device is retracted proximally from the site of delivery, sheath 600 engaged by hook 602 is also retracted proximally leaving stent 108 to self expend to a pre-configured diameter, D2.

The sheath may also have drainage ports 604 or purge holes formed in the wall near the area covering the stent. There may be a single hole or multiple holes, e.g. three holes, formed, which allow fluids, e.g. saline, to readily escape. The stent may also be configured to expand upon the application of an electric current actuated from a location external of the patient. The current may be delivered to the stent via an electrical connection or line (not shown) disposed within the body of a guidewire.

Once the stent has been released from the cage and expanded to contact the walls of the desired body lumen, the guidewire and sheath may be withdrawn into the body of the optional catheter and removed entirely therefrom, or, the optional catheter may itself be withdrawn from the body of the patient. If only a guidewire is used, the guidewire and caged device having the sheath engaged by a hook therein, may be removed from the patient's body in a similar fashion. If the optional catheter is employed and it is desirable to remove only the guidewire, the optional catheter may be left in position within the body lumen to allow for the insertion of additional tools or the application of drugs near the treatment site.

As shown in FIG. 7, a slit or port 700 may be provided on an optional rapid exchange type catheter such that the guidewire 116 can exit it at a point proximal to tubular portion 102. In this way guidewire 116 need not exit the device at the proximal end of the optional catheter. Given the much shorter guidewire exchange length afforded by the slit, the caged delivery device and any other apparatus can be threaded onto and advanced along the guidewire with greater ease, and in significantly shorter times. Similarly, devices can be more quickly and conveniently withdrawn while maintaining guidewire in place, since the exchange portion manipulated by a physician is close to the point of entry into the patient. Insertion and removal is thus facilitated by the shorter length over which the guidewire and devices are in contact with one another and friction between these components is reduced.

The caged delivery device described herein further contemplates stent delivery using an expandable balloon catheter. In this variation (not shown), a stent in its constricted form is delivered, positioned, and released from the cage in the manner described above. Deployment however, is accomplished by sliding a balloon catheter tube distally through the lumen of the stent. Pressure is then provided (e.g. introducing a pressurized saline solution into the lumen of the catheter) to expand the dilation balloon located on the catheter. As the balloon expands the stent expands radially into its finally diametric form, D2. Once the deployment is complete, the balloon is deflated (e.g. by applying a vacuum to the balloon inflation lumen) and the entire device withdrawn. As described above, the guidewire may or may not be withdrawn.

However, as previously mentioned, caged stent delivery device 100 may be used without optional catheter 118 as well. For example, in tortuous pathways having small circumferential lumens, such as intracranial vessels, the caged stent delivery device may be used with guidewire 116 alone if the body of optional catheter 118 presents too large a cross section for delivery purposes. In this variation, the proximal end of tubular portion 102 is attached to a distal portion of guidewire 116 as shown in FIG. 8. The stent may be loaded onto the guidewire after attachment to the tubular portion, or the guidewire may already have a stent loaded thereon, as described in Applicant's co-pending application, U.S. Ser. No. 10/087,127 Entitled, "Guidewire Loaded Stent for Delivery Through a Catheter" filed for on Feb. 28, 2002, which is hereby incorporated by reference in its entirety. As shown in FIG. 12, the stent 308 is loaded on a tapered portion 312 of guidewire 10. In the embodiment of FIG. 13, stent 318 is loaded on a reduced diameter stepped section 332 of guidewire 330.

Any number of suitable methods may be used to attach the proximal end of tubular portion 102 to the distal end of guidewire 116. A few variations are illustrated in FIGS. 9A-9M. For example, in one variation (not shown) tubular portion 102 of the caged delivery device is comprised of a low-temperature heat shrink material. The caged delivery device is then attached to distal end of guidewire 116 by heating tubular portion 102 until it constricts, thereby tightly attaching itself to guidewire 116.

Figure 9A:
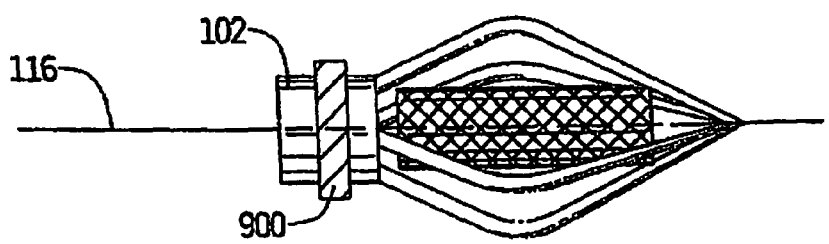
Figure 9B:
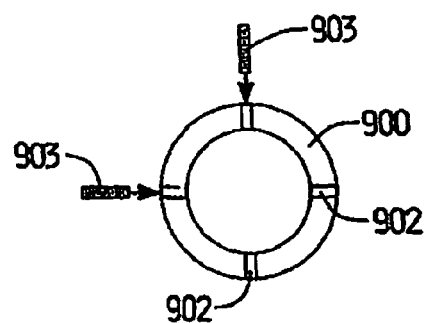

In another variation, shown in FIG. 9A, a locking collet 900 is used to attach tubular portion 102 to guidewire 116. In this variation, locking collet 900 surrounds a section of tubular portion 102. Optional set screws 903 may be inserted into set screw holes 902 to tighten the collet onto the tubular portion and secure the guidewire therein. Another variation is shown in FIGS. 9B and 9C where an internal socket 904 with or without a set screw or locking mechanism may be used. As illustrated in FIG. 9D, socket 904 fits within the lumen of tubular portion 102 and is configured to confine guidewire 116 therein. FIG. 9C illustrates how a set screw 906 may be inserted into a set screw hole 908 located on tubular portion 102. Set screw hole 908 is accessible from the outer surface of tubular member and extends inwardly to contact guidewire 116 such that when set screw 906 is inserted into set screw hole 908, socket 904 is tightened and guidewire 116 secured therein. Any number of set screws and corresponding set screw holes may be used.

In another variation, a locking ball mechanism 910 is used as shown in FIG. 9D. In this variation, a ball 914 with limited freedom of movement is confined within a wedged shaped cavity section 912 within locking ball mechanism 910. Locking ball mechanism 910 is configured such that when pushed forward distally, ball 914 becomes wedged in wedged portion 912 thereby contacting and engaging guidewire 116. The ball may be released by pulling the locking mechanism backward proximally. In this manner, the guidewire may be withdrawn from tubular portion 102 by pulling the tubular portion proximally off the proximal end of guidewire 116.

In yet another variation, shown in FIG. 9J the tubular portion is crimped onto the guidewire using a hemostat or similar device. Another variation is shown in FIGS. 9K and 9L where tubular portion 102 is made of silicone or similar flexible material. In this variation, tubular portion 102 may simply be rolled on and off of guidewire 116. In another variation, shown in FIG. 9G, at least a portion of the inner surface of tubular portion 102 has a cutting or a flared edge 916. Cutting edge 916 may be located at the proximal tip of tubular portion 102, as shown in FIG. 9G, or alternatively, may be located at any distance along the inner surface of tubular portion 102. In a similar fashion, the inner surface of tubular portion 102 may be serrated or textured to facilitate griping the guidewire 116 within the lumen of the tubular portion. In yet another variation (not shown), the tubular portion is simply attached to the guidewire by use of an adhesive, for example, Loctite glue.

Once the caged device is attached to the guidewire-loaded stent, it is ready for use. Then, for example, the guidewire-loaded stent, having the caged delivery device positioned near its distal end may be advanced within a body lumen to a treatment site, e.g., an aneurysm. Once the guidewire has reached a location near the aneurysm (monitoring of the location may be accomplished via use of radio-opaque techniques) the caged device is positioned over the neck of the aneurysm. Then, the cage is opened, the stent is released, and the stent is left to radially self expand in gentle contact with the vascular walls, occluding the neck of the aneurysm. Similarly, when a sheath is employed, the sheath is retracted proximally as described above, thus exposing the stent to the vascular environment. However, should it become necessary or desirable to do so, the stent may be recaptured within the caged delivery device in a similar manner as described above. In this way, the stent can be repositioned and redeployed.

In another variation, illustrated by FIG. 10, use of the guidewire loaded stent and caged delivery device employs an outer sheath. In this variation, a sheath 1000 is positioned around the outer surface of cage 106, surrounding at least a portion thereby and enveloping the cage and stent therein. In this way, delivery device 100 and stent 108, maintain a very low profile while maneuvering through small and tortuous pathways.

This variation may have any number of configurations. For example, the caged delivery device and outer sheath 1000 may take the form of a single unit. Alternatively, the outer sheath may be separate from the caged delivery device, but adaptable thereto. In one variation, sheath 1000 is configured such that it can be "snap-fit" onto the outer surface of cage 106. The sheath may be constructed of any number of materials, be of any length, and be sterilizable. The sheath may further comprise radio-opaque markers, or be constructed of radio-opaque material. After the stent is delivery to the treatment site, the outer sheath may be retracted in a manner analogous to that described above. The arms may then be opened, and the stent deployed.

FIG. 11 shows another variation of the present invention in which the guidewire loaded stent has safety holes 1100. In this variation arms 104 are insertable into safety holes 1100 to further secure them in a first, delivery position. In this way, grater confidence may be provided that the device and stent will retain a low profile during delivery. The arms 104 may be of equal length or be of different lengths. As described above, having arms of different lengths helps facilitate controlled release and deployment of the stent. The location of safety holes 1100 is determined by the length of arms 104, and are located a distance along the guidewire at a position corresponding to the distal tip of the arms.

It should be understood that the applications of the cage stent delivery device and methods of use discussed herein are not limited to the deployment and use within the vascular system but may include any number of further treatment applications. Other treatment sites may include areas or regions of the body such as organ bodies. Modification of the above-described assemblies and methods for carrying out the invention, and variations of aspects of the invention that are apparent to those of skill in the art and intended to be within the scope of the claims.

What we claim is:

1. In combination a device for delivering a stent within an intraluminal cavity and a stent comprising:
    a guidewire having a proximal end and a distal end;
    a stent mounted on and carded by the guidewire, the stent movable between a smaller diameter delivery position and an expanded placement position, and having a proximal portion an intermediate portion and a distal portion;
    a tubular portion fixedly attached to the distal portion of the guidewire, the guidewire and the attached tubular portion advanceable together intraluminally to deliver the stent to a surgical site; and
    at least two arms extending from the tubular portion and extending in a distal direction, the arms encircling portion of the guidewire when the tubular portion is attached to the guidewire, the arms advanceable together with the guidewire to the surgical site and the guidewire extending between the arms, the arms movable to pivot between an initial closed stent constraining position to retain the stent for delivery and a subsequent open stent release position to place the stent at the surgical site, each arm engages the proximal portion and the distal portion of the stent to surround the stent and constrain the stent on the guidewire in the initial closed stent constraining position for delivery of the stent to the surgical site, the arms having free ends movable toward and away from each other between the closed position to constrain the stent and to the subsequent open stent release position to release the stent from the guidewire for expansion and placement at the surgical site.

2. The combination of claim 1, wherein the arms are normally in the closed stent constraining position, the arms being urged against their closed stent constraining position to the open stent release position wherein the free ends of the arms are spaced a greater distance apart than in the closed stent constraining position to open the arms to release the stent for movement of the stent to the expanded placement position.

3. The combination of claim 2, further comprising a mechanism for controllably moving the arms radially a distance from one another to move the arms between the closed stent constraining position and the open stent release position.

4. The combination of claim 3, further comprising an outer sheath, wherein the outer sheath constrains the stent and retraction of the sheath enables the stent to expand.

5. The combination of claim 1, wherein the tubular portion comprises a heat shrink material and the arms are attached to the guidewire by heating the tubular portion until it constricts.

6. The combination of claim 1, further comprising a locking collet surrounding a section of the tubular portion to connect the tubular portion to the guidewire.

7. The combination of claim 1, further comprising a locking mechanism, the locking mechanism slidable to wedge in the guidewire.

8. The combination of claim 1, wherein the tubular portion has a sharp surface or textured surface to engage an outer surface of the guidewire.

9. The combination of claim 1, further comprising an outer sheath, wherein the outer sheath constrains the stent and retraction of the sheath enables the stent to expand.

10. The combination of claim 9, wherein the sheath includes a radiopaque marker.

11. The combination of claim 9, wherein the sheath is positioned over the arms.

12. The combination of claim 1, wherein the stent is mounted on a reduced diameter portion of the guidewire.

13. The combination of claim 12, wherein the reduced diameter portion of the guidewire comprises a tapered portion.

14. The combination of claim 1, wherein the arms have a proximal section and a distal section defined along their length to constrain the respective proximal portion and distal portion of the stent as the arms extend beyond the midpoint of the stent to constrain the stent.

15. The combination of claim 1, wherein at least one radiopaque marker is located on the arms.

16. The combination of claim 1, wherein the arms are constructed of a radio-paque material.

17. The combination of claim 2, wherein the arms are flexible such that a cage defined by the arms is expandable and collapsible as the arms extend over a substantial portion of the stent to encapsulate the stent.

18. The combination of claim 17, wherein the arms are further movable toward the closed stent constraining position to recapture the stent within the cage.

\* \* \* \* \*